United States Patent [19]

Cosby et al.

[11] 4,115,433

[45] Sep. 19, 1978

[54] CATALYST AND PROCESS FOR PRODUCING POLYHYDRIC ALCOHOLS AND DERIVATIVES

[75] Inventors: Lowell Alan Cosby; Rocco Anthony Fiato; José Luis Vidal, all of Charleston, W. Va.

[73] Assignee: Union Carbide Corporation, New York, N.Y.

[21] Appl. No.: 840,866

[22] Filed: Oct. 11, 1977

[51] Int. Cl.$^2$ .................... C07C 27/06; C07C 29/16
[52] U.S. Cl. ...................... 260/449 L; 260/449 R; 260/449.5; 260/429 R; 423/417; 252/439
[58] Field of Search ............ 260/449 R, 449 L, 449.5

[56] References Cited

U.S. PATENT DOCUMENTS

| | | | |
|---|---|---|---|
| 3,957,857 | 5/1976 | Pruett et al. | 260/449 R |
| 3,968,136 | 7/1976 | Walker et al. | 260/449 R |

*Primary Examiner*—Howard T. Mars
*Attorney, Agent, or Firm*—Donald M. Papuga

[57] ABSTRACT

A novel catalyst and process for the manufacture of polyhydric alcohols from synthesis gas. This novel catalyst is a rhodium carbonyl sulfur cluster compound. In particular, the anion cluster of the rhodium carbonyl sulfur compound is of the following empirical formula:

$$[Rh_{17}(S)_2(CO)_{32}]^{-3}$$

17 Claims, No Drawings

CATALYST AND PROCESS FOR PRODUCING POLYHYDRIC ALCOHOLS AND DERIVATIVES

This invention relates to the production of polyhydric alcohols, in particular alkane polyols, as well as a variety of other chemicals, in particular methanol. The invention is also concerned with a novel catalyst for producing such products from synthesis gas, i.e., a mixture of carbon monoxide and hydrogen.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making alkane diols, triols, tetraols, etc., containing 2, 3, 4 or more carbon atoms. A key product of the process of this invention is ethylene glycol. By-products of this invention are the lesser valuable, but nonetheless valuable, monohydric alkanols such as methanol, ethanol and propanol. The products of the process of this invention contain carbon, hydrogen and oxygen.

There are described in U.S. Pat. No. 3,833,634 issued Sept. 3, 1974, and U.S. Pat. No. 3,957,857, issued May 18, 1976, processes for reacting hydrogen and oxides of carbon in the presence of rhodium carbonyl complex catalysts. U.S. Pat. No. 3,957,857 is concerned with a rhodium carbonyl complex which is a rhodium carbonyl cluster exhibiting a particular infrared spectrum. The conditions, broadly speaking, employed in those processes involve reacting a mixture of an oxide of carbon and hydrogen with a catalytic amount of rhodium in complex combination with carbon monoxide, at a temperature of between about 100° C. to about 375° C. and a pressure of between about 500 p.s.i.a. to about 50,000 p.s.i.a. As described in these patents, the process is carried out in a homogeneous liquid phase mixture in the presence of one or more ligands selected from among groups referred to in the patent, as organic oxygen ligands, organic nitrogen ligands and organic aza-oxa ligands. In addition to the aforementioned U.S. patents, the following U.S. patents and U.S. patent applications amplify the development of the processes for making alkane polyols from mixtures of hydrogen and oxides of carbon:

| | |
|---|---|
| U.S.P. 3,878,292 | Patented April 15, 1975 |
| U.S.P. 3,878,290 | Patented April 15, 1975 |
| U.S.P. 3,878,214 | Patented April 15, 1975 |
| U.S.P. 3,886,364 | Patented May 27, 1975 |
| U.S.P. 3,940,432 | Patented February 24, 1976 |
| U.S.P. 3,929,969 | Patented December 30, 1975 |
| U.S.P. 3,952,039 | Patented April 20, 1976 |
| U.S.P. 3,948,965 | Patented April 6, 1976 |
| U.S.P. 3,944,588 | Patented March 16, 1976 |
| U.S.P. 3,957,857 | Patented May 18, 1976 |
| U.S. Ser. No. 455,380 | Filed March 27, 1974 |
| U.S. Ser. No. 455,379 | Filed March 27, 1974 |
| U.S. Ser. No. 526,942 | Filed November 25, 1974 |
| U.S. Ser. No. 488,139 | Filed July 12, 1974 |
| U.S. Ser. No. 488,140 | Filed July 12, 1974 |
| U.S. Ser. No. 506,862 | Filed September 17, 1974 |
| U.S. Ser. No. 506,864 | Filed September 17, 1974 |
| U.S. Ser. No. 506,865 | Filed September 17, 1974 |
| U.S. Ser. No. 511,740 | Filed October 3, 1974 |
| U.S. Ser. No. 615,093 | Filed September 19, 1975 |
| U.S. Ser. No. 537,885 | Filed January 2, 1975 |
| U.S. Ser. No. 618,023 | Filed September 30, 1975 |
| U.S. Ser. No. 618,061 | Filed September 30, 1975 |
| U.S. Ser. No. 618,021 | Filed September 30, 1975 |
| U.S. Ser. No. 727,646 | Filed September 29, 1976 |
| U.S. Ser. No. 782,986 | Filed March 30, 1977 |

This invention constitutes an addition to or an improvement of the inventions of the foregoing patents and patent applications.

It has been found that the rhodium carbonyl sulfur cluster compound of the present invention is an effective catalyst for the production of polyhydric alcohol(s) from synthesis gas. Moreover, the rhodium carbonyl sulfur clusters of this invention are almost unique in their stability when employed as a catalyst for the production of alkane polyols from the homogeneous catalytic reaction of synthesis gas. They are not as dependent upon solvent selection in carrying out this process to avoid catalyst losses. Thus rhodium cluster stability in the reaction can be achieved with a greater variety of solvents, even in the recovery of the alkane polyol in the recovery phase.

The novel rhodium carbonyl sulfur cluster compound of the present invention is a combination of a cluster anion associated with a cation.

P. Chini, in a review article entitled "The Closed Metal Carbonyl Clusters" published in Review (1968), Inorganic Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster."

The rhodium carbonyl sulfur cluster anion of this invention is believed to contain two sulfur and one rhodium atom inside the cluster's cage. The two sulfur atoms are bonded to four rhodium atoms and to the central rhodium atoms. The central rhodium atom is bonded to eight other rhodium atoms and these and each one of the other eight rhodium atoms are coordinated to a terminal and two bridging carbonyls.

This rhodium carbonyl sulfur cluster anion is characterized by the following empirical formula:

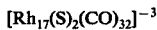

$[Rh_{17}(S)_2(CO)_{32}]^{-3}$

Under pressure conditions in the homogeneous liquid phase, in the presence of $H_2$ and CO, the cluster exhibits an infrared spectral pattern which is characterized by three significant infrared bands at about 2010 cm$^{-1}$, about 1845 cm$^{-1}$, and about 1810 cm$^{-1}$, each plus or minus 10 cm$^{-1}$.

The cations which may be used with the rhodium carbonyl sulfur anion include alkali metal and alkaline earth metal cations, organic cations such as $[(C_6H_5)_3P]_2N^+$, $R_4N^+$, $R_{4-n}R_nN^+$, wherein R is alkyl or aryl and n is a positive integer from 0 to 4, and other positively charged species that would form a salt with $[R_{17}S_2(CO)_{32}]^{-3}$. The preferred cations include $K^+$, $Cs^+$, $NH_4^+$ and $[C_6H_5CH_2N(C_2H_5)_3]^+$.

The cations are generally added to the reaction in the form of salts. Illustrative salts which are useful in the practice of this invention are the ammonium salts and the salts of the metals of Group I and Group II of the Periodic Table (Handbook of Chemistry and Physics — 50th Edition), for instance the halide, hydroxide, alkoxide, phenoxide and carboxylate salts such as sodium fluoride, cesium fluoride, cesium pyridinolate, cesium formate, cesium acetate, cesium benzoate, cesium p- methylsulfonyl-benzoate $(CH_3SO_2C_6H_4COO)Cs$, rubidium acetate, magnesium acetate, strontium acetate, ammonium formate, ammonium benzoate and the like. Preferred are the cesium and ammonium carboxylate salts, most preferably their formate, benzoate and para-lower alkyl sulfonyl benzoate salts.

Also useful in the practice of the present invention are organic salts of the following formula:

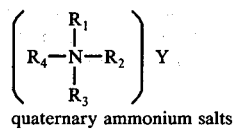
quaternary ammonium salts

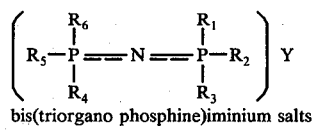
bis(triorgano phosphine)iminium salts wherein $R_1$ through $R_6$ in formulas (I) to (II) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1] heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $-(C_nH_{2n}O)_xOR$ wherein $n$ has an average value from 1 to 4, $x$ has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas (I) and (II) above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas (I) and (II), above, is a carboxylate, most preferably formate, acetate and benzoate.

A suitable method for preparing the bis(triorganophosphine) iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

Under reaction conditions the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The process of this invention which involves the reaction between carbon monoxide and hydrogen in the homogeneous liquid phase mixture, is carried out at a temperature of between about 210° C. to about 320° C., and preferably between about 260° C. to about 280° C. sufficient to produce the alkane polyol. The process is also conducted under superatmospheric pressure. Pressures of from about 1,000 pounds per square inch absolute (psia) to about 50,000 psia, and higher, can be employed but with no apparent advantages attendant thereto which offset the unattractive plant investment outlay required for such high pressure equipment. Preferably, pressures in the range of about 8,000 psia to about 20,000 psia are utilized.

In practising in the process of this invention, the reaction (or residence) time utilizing the catalyst system, as aforedescribed, can range from about fractions of a second to as long as 3 to 4 hours or more, depending upon the conditions selected; milder conditions providing longer residence times whereas more aggressive conditions in terms of pressure and temperature reducing the residence time.

The reaction is effected with a normally liquid organic solvent such as are described in U.S. Pat. Nos. 3,833,634 and 3,957,857. The description of solvents as contained in those patents are incorporated herein by reference. Also, the crown ethers are suitable herein, particularly those as described in U.S. patent application Ser. No. 832,384 filed Sept. 13, 1977, which application is incorporated herein by reference. The crown ethers described therein contain at least four oxygen heteroatoms and include [18]-crown-6 and [15]-crown-5.

The preferred solvents for practising the invention are a number of solvents which have heretofore been described in the production of alkane polyols from synthesis gas.

However, the solvents should not contain sulfur, since sulfur tends to destroy the cluster compound of the present invention. Particularly desirable solvents are tetraglyme, gamma-butyrolactone and the crown ethers, for example, [18]-crown-6. Other very desirable solvents include mixtures of crown ethers and tetraglyme, mixtures of crown ethers and gamma butyrolactone.

The $[Rh_{17}(S)_2(CO)_{32}]^{-3}$ anion is obtainable by the following procedure:

$Rh(CO)_2AcAc*$(12.0 g., 46.2 mmoles) is dissolved in 800 ml. of tetraglyme, to which a solution of cesium benzoate (2.40 g., 9.45 mmoles) in a polar solvent such as methanol, water or ethylene glycol (40 ml.) is added. A potential sulfur ligand is added to the system to give a rhodium to sulfur weight ratio of approximately 20. In those cases tested, $H_2S$ and $SO_2$ have been measured into a vacuum line and condensed directly into the remaining 200 ml. of tetraglyme. Both solutions are mixed and stirred overnight. The resulting solution is charged to a previously nitrogen purged high pressure stirred autoclave which is pressurized with carbon monoxide and hydrogen (1:1) to 4000–8000 psig and heated to 120°–250°. The solution is allowed to react overnight. The solution is then removed from the autoclave and filtered. The filtrate is [Rh$_{17}$(S)$_2$(CO)$_{32}$]$^{-3}$.

*AcAc means acetylacetonate.

The quantity of cluster compound employed is not narrowly critical and can vary over a wide range. In general, the process of preparing alkane diols and derivatives thereof is desirably conducted in the presence of a catalytically effective quantity of the cluster compound which gives a suitable and reasonable reaction rate. Reaction proceeds when employing as little as about 1 × 10$^{-6}$ weight percent, and even lesser amounts, of rhodium (calculated as the metal in the cluster compound) based on the total weight of reaction mixture. The upper concentration limit can be quite high, e.g., about one weight percent rhodium and higher, and the realistic upper limit in practicing the invention appears to be dictated and controlled more by economics in view of the exceedingly high cost of rhodium metal and rhodium compounds. No particular advantages at relatively high concentrations or rhodium are manifest. Depending on various factors such as the partial pressures of oxides of carbon and hydrogen, the total operative pressure of the system, the operative temperature, the choice of the normally-liquid diluent, and other considerations, a cluster concentration of from about 1 × 10$^{-5}$ to about 10 weight percent rhodium (contained in the complex catalyst) based on the total weight of reaction mixture, is generally desirable in the practice of the invention.

A number of nitrogen containing bases may be used in the catalytic process of the present invention. For the purposes of this invention these nitrogen containing bases can be considered to promote the activity of the instant rhodium catalyst.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino(—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

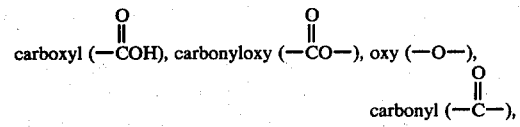

etc., all of said groups containing Lewis base oxygen atoms. In this respect, it is the "hydroxyl" oxygen in the

and the "oxy" oxygen in the

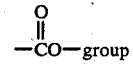

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediamine-tetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amine are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention are promoters, as in the case of an amide, such as formamide, cyanamide, and urea, or an oxime. Further illustrative of these Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; alphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthyl, amine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylamino-naphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2;-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo [2.2.2]octane, purine and the like.

Also included herein are the use of dimorpholine compounds as described in U.S. patent application Ser. No. 727,645, filed Sept. 29, 1976, which description is incorporated herein by reference.

The promoter provided to the reaction mixture is present in an amount which is equal to or greater than that amount, determined from the promoter's basicity, which achieves the optimum rate of formation of said alkane polyol at said correlated catalyst concentration, temperature and pressure of such reaction mixture as described in commonly assigned copending applications Ser. No. 790,653, filed Apr. 25, 1977 and Ser. No. 618,023, filed Sept. 30, 1975, which are incorporated herein by reference.

The concentration of the promoter will typically be within about 0.001 to about 10 molar. Obviously this range is definitive of the potential scatter of concentrations predicated on the varieties of promoter basicity available.

Under reaction conditions the promoter is preferably used in amounts from about 0.02 to about 40 equivalents of promoter, most preferably from about 0.1 to about 20 equivalent of promoter, for every atom of rhodium in the reaction mixture. The number of equivalents of promoter is equal to the number of atoms of promoter times the number of nitrogen atoms in each molecule.

In practicing the novel method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active form of the rhodium carbonyl sulfur cluster may be prepared by various techniques as heretofore described. They can be performed and then introduced into the reaction zone or they can be formed in situ.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857, the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably, the oxide of carbon is carbon monoxide.

The following examples are merely illustrative and are not presented as a definition of the limits of the invention:

EXAMPLE 1

Preparative Method and Analytical Results For [C₆H₅CH₂N(CH₂CH₃)₃]₃[Rh₁₇(S)₂(CO)₃₂]

Rh(CO)₂AcAc*(12.0 g, 46.3 mmoles) is dissolved in 500 ml tetraglyme containing cesium benzoate (2.42 g, 9.53 mmoles) previously dissolved in 5cc. of either water or methanol. H₂S or SO₂(6.05 mmoles) is measured in a vacuum line and condensed into an evacuated round bottom flask containing 500 ml of tetraglyme. Both solutions are mixed and the resulting mixture is charged to a previously evacuated high pressure stirred autoclave, which is then pressurized to 300 atmospheres with a 1:1 mixture of carbon monoxide and hydrogen previously prepared in a gas mixing autoclave. The system is heated to 160°–180° C. and maintained at those conditions overnight.

*"AcAc" means acetylacetonate.

The final solution is collected into a 1500 ml nitrogen purged Schlenck receiver and filtered to remove any insoluble residue. The filtrate is mixed with benzene (12:1 ratio) and allowed to stand overnight. The precipitated oil, left after solvent decantation, is rhodium carbonyl sulfur anion and it is redissolved in isopropanol. This alcoholic solution is column chromatographed with a silica gel column. This solution is then treated with 250cc of an isopropanol solution of benzyltriethylammonium chloride (1.0 g for every 15.0 ml). The red-violet solid precipitate which is the benzyltriethyl-ammonium salt (6.52 g) is collected by filtering. The salt is washed on the filter with fresh isopropanol (5×10 ml). Yield is 72.8%.

The benzyltriethylammonium salt is dissolved in acetone. The acetone solution is placed in a Schlenck receiver which is placed at a 45° angle from the vertical. Isopropanol is added slowly with a constant rate dropping funnel until two layers are formed. The system is placed under a nitrogen atmosphene until crystals grow (about one week). The solvent is decanted and the crystals are washed with isopropanol and vacuum dried.

Elemental analysis of the benzyltriethyl-ammonium salt of decahepta rhodium di-sulfur tri-aconta-di-carbonyl tri anion is as follows:

|   | % Calc. | % Found[1] |   |
|---|---|---|---|
| C | 25.92 | 26.00; | 25.95 |
| H | 2.02 | 2.02; | 2.08 |
| N | 1.28 | 1.51; | 1.43 |
| Rh | 53.26 | 53.06; | 53.23 |
| S | 1.95 | 2.08; | 2.02 |

[1]Samples were analyzed twice.

EXAMPLE 2

The procedure of Example I is repeated exactly with the exception that the resulting tetraglyme solution is added to an equivalent volume of a 1:1 volume mixture of water and [18]-crown-6-ether.

The elemental analysis of the product which is the cesium salt of $[Rh_{17}(S)_2(CO)_{32}]^{-3}$ is as follows:

|   | % Calc. | % Found[1] |   |
|---|---|---|---|
| C | 26.6 | 30.99; | 30.92 |
| H | 3.09 | 4.00; | 4.01 |
| N | nil | nil; | 0.02 |
| Rh | 37.26 | 37.82; | 37.26 |
| S | 1.37 | 0.88; | 1.00 |

-continued

|   | % Calc. | % Found[1] |   |
|---|---|---|---|
| Cs | 8.49 | 7.96; | 8.12 |

[1]Samples were analyzed twice.

EXAMPLE 3

A 150 ml. capacity stainless steel reactor capable of withstanding pressures up to 7,000 atmospheres was charged with a premix of 75 cubic centimeters (cc) of [18]-crown-6 ether and 1.5 millimoles (mmol) of rhodium supplied to the reaction as the cesium salt of a rhodium carbonyl sulfur cluster compound where the anion cluster is of the following empirical formula:

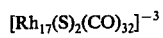

$[Rh_{17}(S)_2(CO)_{32}]^{-3}$ and 7.0 millimoles (mmol) of N-methylmorpholine. The reactor was sealed and charged with a gaseous mixture, containing equal molar amounts of carbon monoxide and hydrogen, to a pressure of 15,000 pounds per square inch (psig). Heat was applied to the reactor and its contents; when the temperature of the mixture inside the reactor reached 280° C., as measured by a suitably placed thermocouple, an additional adjustment of carbon monoxide and hydrogen (H₂:CO=1:1 mole ratio) was made to bring the pressure back to 8000 psig. The temperature (in ° C.) was maintained at the desired value for 4 hours. During this period of time additional carbon monoxide and hydrogen was added whenever the pressure inside the reactor dropped below about 14,500 psig. With these added repressurizations the pressure inside the reactor was maintained at 15,000 psig ± 400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlett Packard FM™ model 810 Research Chromatograph.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for the experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values recited below are the percent rhodium based on the total rhodium charged to the reactor that is soluble or suspended in the reaction mixture plus the was after the specified time.

The temperature, pressure, analysis of the product mixture and rhodium recovery (percent of initial charge) are set forth in TABLE I.

EXAMPLES 4 TO 10

The same equipment and procedure used in Example 3 were used in all the Examples except that cesium benzoate was added to the reaction mixture and except for the conditions specified.

The temperature, pressure, amount of cesium benzoate charged to the reaction, analysis of the product mixture and rhodium recovery are set forth in TABLE I.

added to the reaction mixture, and except that the N-methylmorpholine was optional.

TABLE I

| Examples | T(° C) | P(psig) | Cesium Benzoate (mmoles) | Rate (Mole, Liter$^{-1}$, Hour$^{-1}$) CH$_3$OH | HOCH$_2$CH$_2$OH | %Rh Recovered In Solution |
|---|---|---|---|---|---|---|
| 3 | 280 | 15,000 | — | 0.44 | 0.77 | 90 |
| 4 | 260 | " | 0.125 | Nil | 0.27 | 101[1] |
| 5 | 260 | " | 0.125 | 0.09 | 0.34 | 96 |
| 6 | 280 | " | 0.125 | 0.89 | 1.34 | 112[1] |
| 7 | 280 | " | 0.125 | 0.59 | 1.30 | 104[1] |
| 8 | 280 | " | 0.250 | 0.76 | 1.20 | 97 |
| 9 | 280 | " | 2.50 | 0.10 | Nil | 104[1] |
| 10 | 280 | " | 0.125 | 0.59 | 1.30 | 104[1] |
| 11 | 280 | " | 0.250 | 0.76 | 1.20 | 97 |
| 12 | 300 | " | 0.125 | 3.67 | 2.39 | 113[1] |

[1]indicates quantitative rhodium recovery.

EXAMPLES 13-20

The same equipment and procedure used in Example 3 were used in all the Examples except that the temperature, pressure and amount of N-methymorpholine were varied.

The temperature, pressure, amount of cesium benzoate, amount of N-methylmorpholine, analysis of the product mixture and rhodium recovery are set forth in Table II.

TABLE II

Effect of Temperature-Pressure on Ethylene Glycol Production With Cs$_3$[Rh$_{17}$(S)$_2$CO$_{32}$] Catalyst

| Examples | T(° C) | P(psig) | Cesium Benzoate (mmoles) | N-MM(mmoles) | Rate (Mole, Liter$^{-1}$, Hour$^{-1}$) CH$_3$OH | HOCH$_2$CH$_2$OH | %Rh Recovered In Solution |
|---|---|---|---|---|---|---|---|
| 13 | 300 | 15,000 | 0.125 | 7.0 | 3.67 | 2.39 | 113[1] |
| 14 | 280 | " | 0.125 | 7.0 | 0.59 | 1.30 | 104[1] |
| 15 | 260 | " | 0.125 | 7.0 | 0.09 | 0.34 | 96 |
| 16 | 280 | 12,500 | 0.125 | 7.0 | 0.46 | 0.69 | 88 |
| 17* | 280 | " | 0.250 | 10.0 | 0.43 | 0.53 | 69 |
| 18* | 260 | " | 0.250 | 10.0 | 0.06 | 0.17 | 78 |
| 19* | 300 | 8,000 | 0.250 | 10.0 | 0.19 | 0.05 | 19 |
| 20 | 280 | " | 0.125 | 7.0 | Nil | Nil | 47 |

*Rh charged at 3.0 mmole level.
[1]indicates quantitative rhodium recovery.
'N-MM = N-methylmorpholine.

EXAMPLES 21-26

The same equipment and procedure used in Example 3 were used in all the Examples except that a salt was The temperature, pressure, salt, N-methylmorpholine content, analysis of the product mixture, and rhodium recovery are set forth in Table III.

TABLE III

Effect of Salts and N-MM* on Glycol Production of Cs$_3$[Rh$_{17}$(S)$_2$(CO)$_{32}$] in [18]-crown-5 ether

| Examples | T(° C) | P(psig) | Salt (mmoles) | N-MM(mmoles)* | Rate (Mole, Liter$^{-1}$, Hour$^{-1}$) CH$_3$OH | HOCH$_2$CH$_2$OH | %Rh Recovered In Solution |
|---|---|---|---|---|---|---|---|
| 21 | 280 | 15,000 | — | 7.0 | 0.44 | 0.77 | 90 |
| 22 | 280 | " | — | — | 0.82 | 0.41 | 76 |
| 23 | 280 | " | Ammonium benzoate (0.125) | 7.0 | 0.68 | 0.81 | 85 |
| 24 | 280 | " | N-methylmorpholine (0.125) benzoic acid | 7.0 | 0.34 | 0.52 | 91 |
| 25 | 280 | " | " | 7.0 | 0.46 | 0.55 | 88 |
| 26 | 280 | " | Ammonium benzoate (0.125) | — | 1.15 | 1.15 | 103[1] |

*N-MM = N-methylmorpholine.
[1]indicates quantitative rhodium recovery.

EXAMPLES 27-39

The same equipment and procedure used in Example 3 were used in all the Examples except that the solvent and cesium benzoate content were varied.

The temperature, pressure, amount of cesium benzoate, the solvent, analysis of the product mixture and rhodium recovery are set forth in Table IV.

TABLE IV

Effect of Solvent on Ethylene glycol Production with Cs$_3$[Rh$_{17}$(S)$_2$(CO)$_{32}$]

| Examples | T° (C) | P(psig) | Cesium Benzoate (mmoles) | Solvent | Rate (Mole, Liter$^{-1}$, Hour$^{-1}$) CH$_3$OH | HOCH$_2$CH$_2$OH | %Rh Recovered In Solvent |
|---|---|---|---|---|---|---|---|
| 27 | 280 | 15,000 | 0.250 | [18]-crown-6 | 0.76 | 1.20 | 97 |
| 28 | " | " | 0.125 | " | 0.89 | 1.34 | 113[1] |

TABLE IV-continued

Effect of Solvent on Ethylene glycol Production with $Cs_3[Rh_{17}(S)_2(CO)_{32}]$

| Examples | T° (C) | P(psig) | Cesium Benzoate (mmoles) | Solvent | Rate (Mole, Liter$^{-1}$, Hour$^{-1}$) CH$_3$OH | HOCH$_2$CH$_2$OH | %Rh Recovered In Solvent |
|---|---|---|---|---|---|---|---|
| 29 | " | " | 0.125 | " | 0.59 | 1.30 | 104[1] |
| 30 | " | " | — | " | 0.44 | 0.77 | 90 |
| 31 | " | " | 0.125 | Tetraglyme-[18]-crown-6 (75-5) | 1.12 | 1.12 | 50 |
| 32 | " | " | 0.125 | " | 1.12 | 1.10 | 47 |
| 33 | " | " | — | " | 0.54 | 0.50 | 22 |
| 34 | " | " | 0.125 | Tetraglyme | 0.31 | 0.32 | 20 |
| 35 | " | " | — | " | 0.52 | 0.36 | 20 |
| 36 | " | " | — | " | 0.12 | 0.10 | 22 |
| 37 | 260 | " | 0.125 | [18]-crown-6 | Nil | 0.27 | 101[1] |
| 38 | " | " | 0.125 | " | 0.09 | 0.34 | 96 |
| 39 | " | " | 0.125 | Tetraglyme-[18]-crown-6 (75-5) | 0.15 | 0.76 | 79 |

[1]indicates quantitative rhodium recovery.

EXAMPLES 40-47

The same equipment and procedure used in Examples 3 were used in all the Examples except that the salt and solvent were varied and a catalyst of the prior art, Rh(CO)Ac Ac, was used in place of the catalyst of the invention.

The temperature, pressure, salt, catalyst, solvent, analysis of the product mixture, and rhodium recovery are set forth in Table V.

TABLE V

| Examples | (T(° C) | P(psig) | Salt (Mmoles) | | Catalyst | Solvent | Rate (Mole,Liter$^{-1}$, Hour$^{-1}$) CH$_3$OH | HOCH$_2$CH$_2$OH | %Rh Recovered In Solution |
|---|---|---|---|---|---|---|---|---|---|
| 40 | 280 | 15,000 | Cesium Benzoate | (0.125) | Rh-S-Cs | [18]-crown-6 | 0.59 | 1.30 | 104[1] |
| 41 | " | " | " | (0.375) | RCA | " | 3.33 | 3.89 | 61 |
| 42 | " | " | " | (0.125) | Rh-S-Cs | Tetraglyme-[18]-crown-6 (75-5) | 1.12 | 1.12 | 50 |
| 43 | " | " | " | (0.375) | RCA | " | 1.75 | 1.88 | 23 |
| 44 | " | " | Potossum Benzoate | (0.125) | Rh-S-K | " | 1.20 | 0.51 | 72 |
| 45 | " | " | " | (0.375) | RCA | " | 0.24 | 0.36 | 14 |
| 46 | 260 | " | Cesium Benzoate | (0.125) | Rh-S-Cs | " | 0.15 | 0.76 | 79 |
| 47 | " | " | " | (0.375 | RCA | " | 0.91 | 1.59 | 76 |

Rh-S-Cs = $[Rh_{17}(S)_2CO_{32}]Cs_3$
RCA = 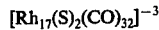AcAc
RH-S-K = $[Rh_{17}(S)_2(CO)_{32}]K_3$
[1]indicate quantitative rhodium recovery

What is claimed is:

1. The process of making an alkane polyol(s) which comprises reacting in a homogeneous liquid phase a mixture of hydrogen and oxides of carbon in the presence of a rhodium carbonyl sulfur cluster compound at a pressure between about 1,000 to about 50,000 pounds per square inch absolute and at a temperature of between about 210° C. and about 320° C. sufficient to form such alkane polyol(s).

2. The process of claim 1 wherein the rhodium carbonyl sulfur cluster compound possesses an infrared spectrum which is characterized by three significant infrared bands between about plus and minus 10 cm$^{-1}$ of about 2010 cm$^{-1}$, about 1845 cm$^{-1}$ and about 1818 cm$^{-1}$.

3. The process of claim 2 wherein the anion of rhodium carbonyl sulfur cluster compound is of the following formula:

$$[Rh_{17}(S)_2(CO)_{32}]^{-3}$$

4. The process of claim 1 wherein the rhodium carbonyl sulfur cluster compound is of the following formula:

$$Cs_3[Rh_{17}(S)_2(CO)_{32}]$$

5. The process of claim 1 wherein the rhodium carbonyl sulfur cluster compound is of the following formula:

$$[C_6H_5CH_2N(C_2H_5)_3]_3[Rh_{17}(S)_2(CO)_{32}]$$

6. The process of claim 1 wherein the rhodium carbonyl cluster compound is dissolved in a solvent.

7. The process of claim 5 wherein the solvent is tetraglyme.

8. The process of claim 5 wherein the solvent is a crown ether.

9. The process of claim 8 wherein the crown ether is [18]-crown-6.

10. The process of claim 5 wherein the solvent is a mixture of tetraglyme and a crown ether.

11. The process of claim 10 wherein the crown ether is [18]-crown-6.

12. The process of claim 1 wherein the temperature of the reaction is between about 260° C. and 280° C.

13. The process of claim 1 wherein the process is conducted under a pressure of between 8,000 to about 20,000 pounds per square inch absolute.

14. The process of claim 1 wherein the alkane polyol is ethylene glycol.

15. The process of claim 1 wherein the principal products recovered are ethylene glycol and methanol.

16. The process of claim 1 wherein the reaction is effected in the presence of a nitrogen containing base promoter.

17. The process of claim 16 wherein the nitrogen containing base promoter is N-methylmorpholine.

* * * * *

UNITED STATES PATENT AND TRADEMARK OFFICE
CERTIFICATE OF CORRECTION

PATENT NO. : 4,115,433
DATED : Sept. 19, 1978
INVENTOR(S) : Lowell Alan Cosby et al.

It is certified that error appears in the above—identified patent and that said Letters Patent is hereby corrected as shown below:

Col. 13, line 58 - "1818" should read --1810--.

Signed and Sealed this

Fifteenth Day of September 1981

[SEAL]

Attest:

GERALD J. MOSSINGHOFF

Attesting Officer     Commissioner of Patents and Trademarks